United States Patent
Spieker et al.

(10) Patent No.: US 10,814,315 B2
(45) Date of Patent: *Oct. 27, 2020

(54) PROCESS FOR MANAGING SULFUR ON CATALYST IN A LIGHT PARAFFIN DEHYDROGENATION PROCESS

(71) Applicant: UOP LLC, Des Plaines, IL (US)

(72) Inventors: Wolfgang A. Spieker, Glenview, IL (US); Adam D. Ballard, Chicago, IL (US); Gregory J. Gajda, Mount Prospect, IL (US); J. W. Adriaan Sachtler, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 40 days.

This patent is subject to a terminal disclaimer.

(21) Appl. No.: 15/847,976

(22) Filed: Dec. 20, 2017

(65) Prior Publication Data
US 2018/0169630 A1  Jun. 21, 2018

Related U.S. Application Data

(60) Provisional application No. 62/436,941, filed on Dec. 20, 2016.

(51) Int. Cl.
*B01J 23/96* (2006.01)
*B01J 38/10* (2006.01)
(Continued)

(52) U.S. Cl.
CPC .............. *B01J 23/96* (2013.01); *B01J 27/045* (2013.01); *B01J 27/30* (2013.01); *B01J 38/02* (2013.01);
(Continued)

(58) Field of Classification Search
CPC ... B01J 23/96; B01J 27/32; B01J 38/02; B01J 38/06; B01J 38/10; B01J 2231/76;
(Continued)

(56) References Cited

U.S. PATENT DOCUMENTS 3,622,520 A * 11/1971 Hayes ................... B01J 27/32
502/37
3,720,602 A   3/1973 Riley et al.
(Continued)

FOREIGN PATENT DOCUMENTS

CN   104107704 B   9/2016
EP     2109502 A2  10/2009
(Continued)

OTHER PUBLICATIONS

PCT Search Report dated Apr. 19, 2018 for corresponding PCT Application No. PCT/US2017/066896.

*Primary Examiner* — Prem C Singh
*Assistant Examiner* — Brandi M Doyle
(74) *Attorney, Agent, or Firm* — Paschall & Associates, LLC; James C. Paschall

(57) ABSTRACT

A process is presented for the management of sulfur on a catalyst. The catalyst is a dehydrogenation catalyst, and sulfur accumulates during the dehydrogenation process. Sulfur compounds are stripped from the spent catalyst and the catalyst is cooled before the regeneration process. The process includes controlling the amount of sulfur that needs to be removed from the catalyst before regeneration.

17 Claims, 2 Drawing Sheets

(51) Int. Cl.
*B01J 38/02* (2006.01)
*C07C 5/333* (2006.01)
*C07C 11/02* (2006.01)
*C10G 45/14* (2006.01)
*C10G 45/04* (2006.01)
*B01J 38/12* (2006.01)
*B01J 27/045* (2006.01)
*B01J 38/06* (2006.01)
*B01J 27/30* (2006.01)

(52) U.S. Cl.
CPC ............... *B01J 38/06* (2013.01); *B01J 38/10* (2013.01); *B01J 38/12* (2013.01); *C07C 5/3337* (2013.01); *C07C 11/02* (2013.01); *C10G 45/04* (2013.01); *C10G 45/14* (2013.01); *B01J 2231/76* (2013.01); *C10G 2300/1085* (2013.01); *C10G 2300/202* (2013.01); *C10G 2300/4093* (2013.01); *C10G 2300/701* (2013.01)

(58) Field of Classification Search
CPC ...... C10G 11/00; C10G 11/182; C10G 35/00; C10G 35/085; C10G 45/04; C10G 45/10; C10G 45/14; C10G 2300/1085; C10G 2300/202; C10G 2300/4093; C10G 2300/701
See application file for complete search history.

(56) References Cited

U.S. PATENT DOCUMENTS

| | | |
|---|---|---|
| 3,907,921 A | 9/1975 | Winter |
| 4,191,633 A | 3/1980 | Dauber |
| 4,377,495 A * | 3/1983 | Tse ............... B01J 23/96 208/140 |
| 4,686,204 A * | 8/1987 | Mester ............ C10G 11/18 502/400 |
| 5,689,033 A | 11/1997 | Forte et al. |
| 5,756,414 A | 5/1998 | Huang et al. |
| 5,880,050 A | 3/1999 | Boitiaux et al. |
| 8,889,579 B2 | 11/2014 | Leonard et al. |
| 2006/0111233 A1* | 5/2006 | Xiao ............... B01J 29/22 502/53 |
| 2013/0252801 A1* | 9/2013 | Leonard ........... B01J 23/96 502/53 |
| 2014/0274673 A1 | 9/2014 | Kauffman et al. |

FOREIGN PATENT DOCUMENTS

| | | |
|---|---|---|
| RU | 2042426 C1 | 8/1995 |
| WO | 2013142044 A2 | 9/2013 |

* cited by examiner

PROCESS FOR MANAGING SULFUR ON CATALYST IN A LIGHT PARAFFIN DEHYDROGENATION PROCESS

CROSS-REFERENCE TO RELATED APPLICATION

This application claims priority from Provisional Application No. 62/436,941 filed Dec. 20, 2016, the contents of which cited application are hereby incorporated by reference in its entirety.

FIELD OF THE INVENTION

The present invention relates to dehydrogenation processes, and in particular to the regeneration of catalysts used in dehydrogenation processes.

BACKGROUND OF THE INVENTION

Light olefins can be produced through the dehydrogenation of light paraffins. The dehydrogenation of paraffins is performed in a catalytic process where a hydrocarbon stream comprising paraffins is contacted with a dehydrogenation catalyst in a reactor under dehydrogenation conditions to generate a light olefin product stream. The catalyst used in this process includes a catalytic metal on a support. The catalytic metal generally comprises a noble metal, such as platinum or palladium. The dehydrogenation process involves many reactions during the dehydrogenation process, the catalyst is slowly deactivated through the reaction process. One of the contributors to the deactivation is the generation of coke on the catalyst. The catalyst therefore, needs to be periodically regenerated to remain useful in the dehydrogenation process. Due to the high temperatures required for the production of light olefins in the dehydrogenation reactors, a low level of $H_2S$ must be maintained in the reactor section to prevent the formation of metal-catalyzed coke. In the case of light paraffin dehydrogenation the sulfur level is controlled by directly injecting a sulfur containing compound such as dimethyl disulfide into the reactor section with the hydrocarbon feed. Sulfur is known to passivate metal surfaces thus preventing metal catalyzed coke formation. The sulfur can be carried into the regenerator by catalyst and over time impact the catalyst performance. This control and regeneration of a catalyst is important for the lifespan of the catalyst and its usefulness in a catalytic process.

SUMMARY OF THE INVENTION

The present invention provides for improved sulfur management in a dehydrogenation reactor system. Sulfur is used for passivation of the metal surfaces to limit metal catalyzed coking. However, sulfur accumulates on the catalyst from sulfur in the feed to the reactors. In some embodiments, the process includes managing the sulfur by removal of the sulfur from spent catalyst by passing the spent catalyst to a sulfur stripping vessel. The sulfur stripping vessel has hot hydrogen gas passed to remove sulfur compounds from the spent catalyst to generate a stripped catalyst stream. The stripped catalyst stream is passed to a cooling section wherein a cooling gas is passed over the catalyst. The catalyst is cooled before sending the stripped catalyst to a regeneration unit. The stripped catalyst is passed to the regeneration unit, and the catalyst is regenerated. The regenerated catalyst is returned to the dehydrogenation reactor system via the reduction zone. In the reduction zone, the regenerated catalyst is contacted with hydrogen to reduce the catalytic metals which are oxidized in the regenerator.

Other objects, advantages and applications of the present invention will become apparent to those skilled in the art from the following detailed description and drawings.

DETAILED DESCRIPTION OF THE INVENTION

Figure 1:
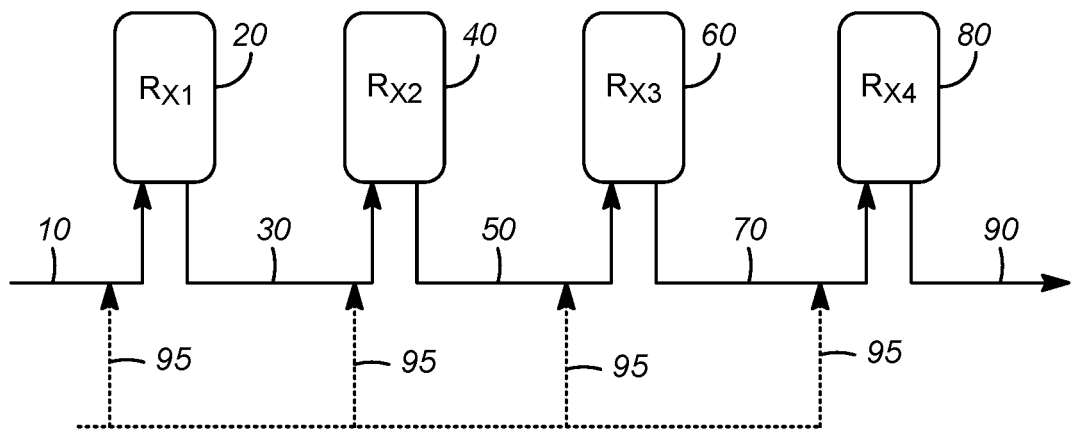
FIG. 1 illustrates water injection to the reactors.

Catalysts are very sensitive to poisons. Catalysts are very expensive, and among the most expensive items in a petrochemical plant. Poisons can accelerate the deactivation of the catalyst, and in some instances the deactivation is sufficient to require catalyst replacement. The controlling of the levels of catalyst poisons in a process can lead to increased catalyst life and improved productivity while generating catalyst savings. In particular, dehydrogenation catalysts that incorporate platinum (Pt) for the active metal component are sensitive to sulfur. While platinum is referred to in the description, it is intended that any platinum group metal can be included in this description. Sulfur is a cause for the accelerated deactivation of dehydrogenation catalysts used in paraffin dehydrogenation, and in particular for platinum based catalysts. However, sulfur is also used to passivate the metal surfaces to limit the metal catalyzed coking. The balance of passivation versus deactivation is important to maintain the useful catalyst life. During the dehydrogenation process, a small amount of sulfur is injected for passivation purposes. The sulfur will build up over time, and will have a significant sulfur concentration on the catalyst which can be as high as 0.1 wt % to 1 wt % on the spent catalyst, or more commonly in the range of 0.1 wt % to 0.5 wt %. Consequently sulfur also needs to be removed to limit the amount of sulfur in the regenerator, reduction zone, and entering the reaction zone.

In a normal process, the catalyst is continuously circulated between the dehydrogenation reactor and the regenerator. The catalyst accumulates coke during the dehydrogenation process and the regenerator burns off the coke and the platinum is re-dispersed over the catalyst surface. Platinum re-dispersion is commonly carried out using a process referred to as oxy-chlorination, wherein the catalyst is contacted with a halogen containing gas at elevated temperatures. The halogen is usually chlorine. The sulfur that is present on the catalyst entering the regenerator is converted from sulfides to sulfates in the burn zone of the regenerator. It has been found that more severe conditions, i.e. higher temperatures and longer residence times, are required to strip sulfate from the catalyst as compared to sulfide using the same hydrogen rich stripping gas. It is therefore desirable to strip sulfur from the catalyst prior to oxygen exposure in the regenerator section where it is converted from sulfide to sulfate. The catalyst exiting the burn zone, and the platinum re-dispersion zone, have been observed to have sulfates present on the catalyst, and to have a surface enrichment of sulfur. This sulfur has also been observed to displace chlorides leading to skewed sulfur profiles and correlating to skewed chloride profiles. There is further evidence that the sulfur contributes to the migration of platinum on the catalyst surface by creating an energy gradient during platinum re-dispersion. This bulk migration leads to platinum migration and accelerated deactivation of the catalyst.

The process often includes contacting the spent catalyst, prior to passing the catalyst to the regenerator, with a reduction zone effluent gas to adsorb chloride stripped from the catalyst in the reduction zone. This reduces the chloride load on the downstream chloride treater and increases the chloride treater adsorbent bed life.

The sulfur that remains on the regenerated catalyst as the catalyst is lifted to the reduction zone is in the form of a sulfate and can be present in a relatively high concentration, ranging from 0.05 wt % to 1 wt % of the catalyst, or more commonly in the range from 0.05 wt % to 0.5 wt %. The sulfate can be reduced to a sulfide and then stripped off the catalyst with hydrogen if the catalyst is heated to an elevated temperature for a sufficient time. One problem with this process is that in the reduction zone, a substantial amount of water and hydrogen sulfide ($H_2S$) is generated. The water, when present in relatively high concentrations, contributes to platinum agglomeration, and the agglomeration reduces the activity of the catalyst. The water, when present in relatively high concentrations, may also impact the interaction of Pt with other catalytic components of the catalyst, adversely impacting the catalyst performance by decreasing activity or increasing side reactions such as coking.

The elevated $H_2S$ concentration in the reduction zone effluent may further degrade the catalyst if it is contacted with the spent catalyst to adsorb HCl that is liberated in the chlorination zone by further increasing the sulfur passed to the regenerator with the catalyst. The problems associated with stripping the sulfate from the catalyst in the reactor section are equally undesirable. One consequence is the potential for a local increase in $H_2S$ and water concentrations which can accelerate corrosion of process equipment and the accumulation of tramp, or undesirable stray, metals on the catalyst. In addition, the water generated by the reduction of sulfate can increase the chloride loss, and therefore increase the chloride concentration in the reactor effluent. This shortens the chloride treater life.

Sulfur is a necessary component of the feedstock, and the sulfur on the catalyst cannot be removed or reduced through simply eliminating the sulfur injection. Sulfur management is important for a long catalyst life. The present invention seeks to improve the sulfur management and avoids the problems associated with high sulfur concentrations in the regenerator and the reduction zone by stripping the sulfur from the spent catalyst before passing the spent catalyst to the regenerator. In some embodiments, the process comprises passing the spent catalyst to a sulfur stripping vessel. However, in some embodiments there is no stripper after the last reactor. In the embodiments with a stripper, a hydrogen rich gas stream is passed to the stripping vessel at an elevated temperature to contact the catalyst and strip sulfur and sulfur compounds from the catalyst, to generate a stripped spent catalyst stream. The stripped spent catalyst stream is passed to a catalyst cooler to cool the catalyst. The catalyst cooler has a cooled gas passed over the catalyst to reduce the temperature of the catalyst before passing the spent catalyst to the regenerator. The stripped spent catalyst stream is passed to the regenerator and a regenerated catalyst stream is generated. The regenerated catalyst is returned to the dehydrogenation reactor via the reduction zone. The reduction zone returns any metal on the catalyst to its metallic state.

The spent catalyst is stripped with a heated hydrogen rich gas stream, where the temperature is at least 150° C., with a preferred temperature greater than 250° C., and a more preferred temperature greater than 300° C. The hydrogen rich stripping gas will contain greater than 50 mol % hydrogen, preferably greater than 80 mol % hydrogen, and more preferably greater than 90 mol % hydrogen. In general, it has been found that for 30 minutes residence time in the sulfur stripping zone, approx. 30% of the sulfide is removed at 150° C., and approx. 85% of the sulfide is removed at 250° C. Increasing the temperature of the gas or the residence time further increases the extent of sulfur removal. The preferred conditions are to have the catalyst reside in the sulfur stripping vessel as a sufficiently high temperature to reduce and remove at least 90% of the sulfur from the catalyst. The residence time in the stripping vessel is related to the temperature for stripping, where as the stripping temperature is increased, the residence time can be reduced. After stripping the catalyst for a sufficient time in the sulfur stripping vessel, the catalyst is passed to a catalyst cooling unit. The catalyst is typically cooled to a temperature less than 200° C. to protect downstream catalyst handling equipment. Preferably, the catalyst is cooled to a temperature between 100° C. and 150° C.

While the stripping and cooling can be performed with different vessels, combining the sections into a single vessel allows for better material handling and reduces the number of process vessels that must be purchased and maintained. When retrofitting of existing dehydrogenation processes separate vessels can be used, where an additional vessel or two can be added at the catalyst outlet of the last reactor in the dehydrogenation reactor system.

In one embodiment, the process includes passing the stripped spent catalyst to a vessel containing a cooling zone, where the catalyst is contacted with the reduction zone effluent. The stripped spent catalyst adsorbs chloride that had been liberated in the reduction zone. While chloride ions are the main halogen ions liberated in this zone, other halogen ions that might be present can also be adsorbed and removed from the catalyst. The stripped and cooled spent catalyst is then passed to the regenerator along with the adsorbed chloride or alternative halogen.

The process can be seen in the FIG. 1. A dehydrogenation process can comprise a plurality of dehydrogenation reactors, or a single dehydrogenation reactor. The system, and process, utilizes a moving bed reactor system, where catalyst flows through the reactors. The catalyst upon leaving a reactor is collected and passed to a subsequent reactor in a reactor system. The catalyst leaving the last reactor is collected and passed to a regeneration system. The example illustrated in FIG. 1 has four reactors. The feed 10 enters the first reactor 20 to produce a first effluent stream 30. The product stream 30 enters the second reactor 40 to produce the second effluent stream 50. The second product stream 50 enters the third reactor 60 to produce the third effluent stream 70. The third product stream 70 enters the fourth reactor 80 to produce the product stream 90. Water may be injected to each of the four reactors. In one embodiment, water will only be injected in the fourth reactor 80. In another embodiment, water will be injected in all of the four reactors. However, it is also contemplated that water may be injected into any combination of the reactors. Water may be in the form of stream, condensate, demineralized water, or demineralized steam.

Figure 2:
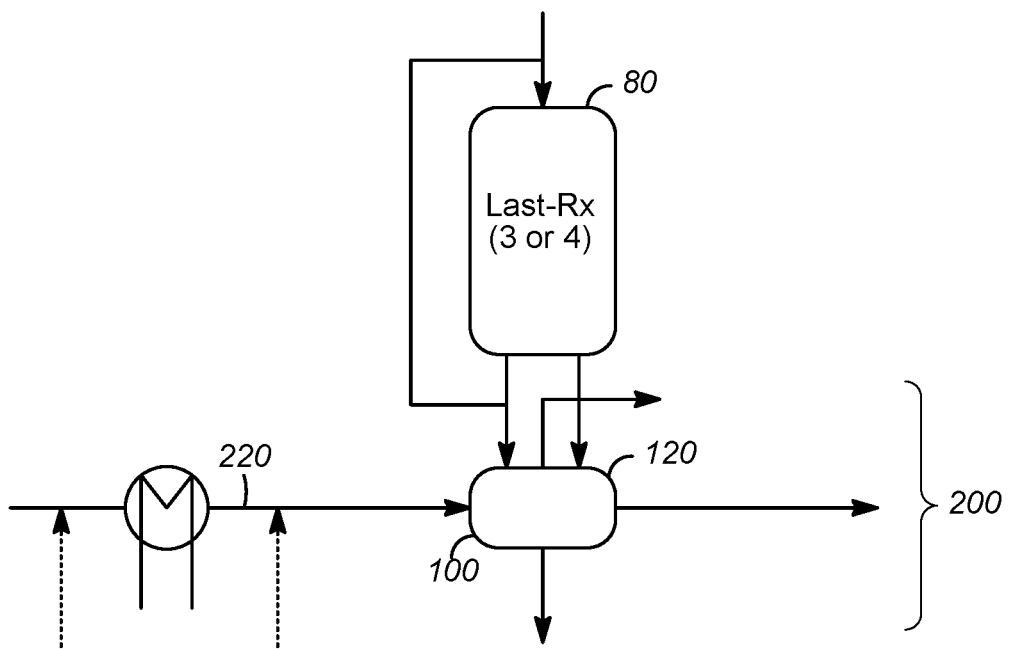
FIG. 2 illustrates water injection to the stripper.

As shown in FIG. 2, before passing the catalyst to the regeneration system, the catalyst leaving the last reactor is passed to a catalyst collector 100, which has been modified for pretreatment of the catalyst before passing the catalyst to the regenerator. The catalyst collector 100 is a combination stripping and cooling vessel. The catalyst collector 100 is positioned in fluid communication with the catalyst outlet from the last reactor, and catalyst flows downward through a first stripping section 200, then to a cooling section. Spent catalyst is passed to the vessel through one or more catalyst entry ports 120, and flows to the stripping section 200. A substantially sulfur free hydrogen rich gas is passed through the stripping gas port 220 to the stripping section 200, removing a portion of the sulfur compounds on the spent catalyst. Preferably, the substantially sulfur free hydrogen rich gas has less than 100 ppm by vol. $H_2S$. The stripped catalyst flows to the cooling section. A cooling gas is passed to the cooling section through a cooling gas port, and flows over the catalyst to cool the catalyst. The cooled catalyst is passed out the cooled catalyst port to a catalyst regenerator. The combined stripping gas and cooling zone effluent is passed out of the vessel through a gas exit port. The catalyst is regenerated in the regenerator and passed back to the first reactor in the dehydrogenation reactor system via the reduction zone. The stripping gas and cooling gas effluents may be combined within the catalyst collector 100 or external to the catalyst collector 100, wherein the vessel includes one or more gas outlets.

The hot stripping gas can be hydrogen generated by the dehydrogenation process and can be heated to a preferred temperature prior to passing the hot gas to the stripping section 200. In an alternative embodiment, the hot stripping gas can be an effluent gas from the reduction zone if the spent catalyst has been sulfur stripped. The cooling gas may be hydrogen generated by the dehydrogenation process and can be cooled to a preferred temperature prior to passing the cooling gas to the cooling zone. In an alternative embodiment, the cooling gas can be an effluent gas from the reduction zone. The regenerated catalyst is passed to the reduction zone prior to being passed to the dehydrogenation reactors. The purpose of the reduction zone is to reduce the catalytic metal on the catalyst prior to passing the catalyst to the dehydrogenation reactors. Excess halogens may be stripped from the catalyst in the reduction zone. Typically, excess chloride is stripped in the form of HCl. By directing the reduction zone effluent gas to the cooling zone, the chloride may be adsorbed on the stripped spent catalyst.

In another embodiment, there may be water injection to both the reaction zone and the stripping zone. In this embodiment, the water may be injected to any or all of the reactors in the reaction zone, and then is also injected to the stripper in the stripping zone.

Optional embodiments include directing the reduction zone effluent to the reactor effluent without contacting the spent catalyst. The effluent gas from the stripping zone and the cooling zone may be directed to the reactor effluent, or to the inlet of any upstream reactor.

Figure 3:
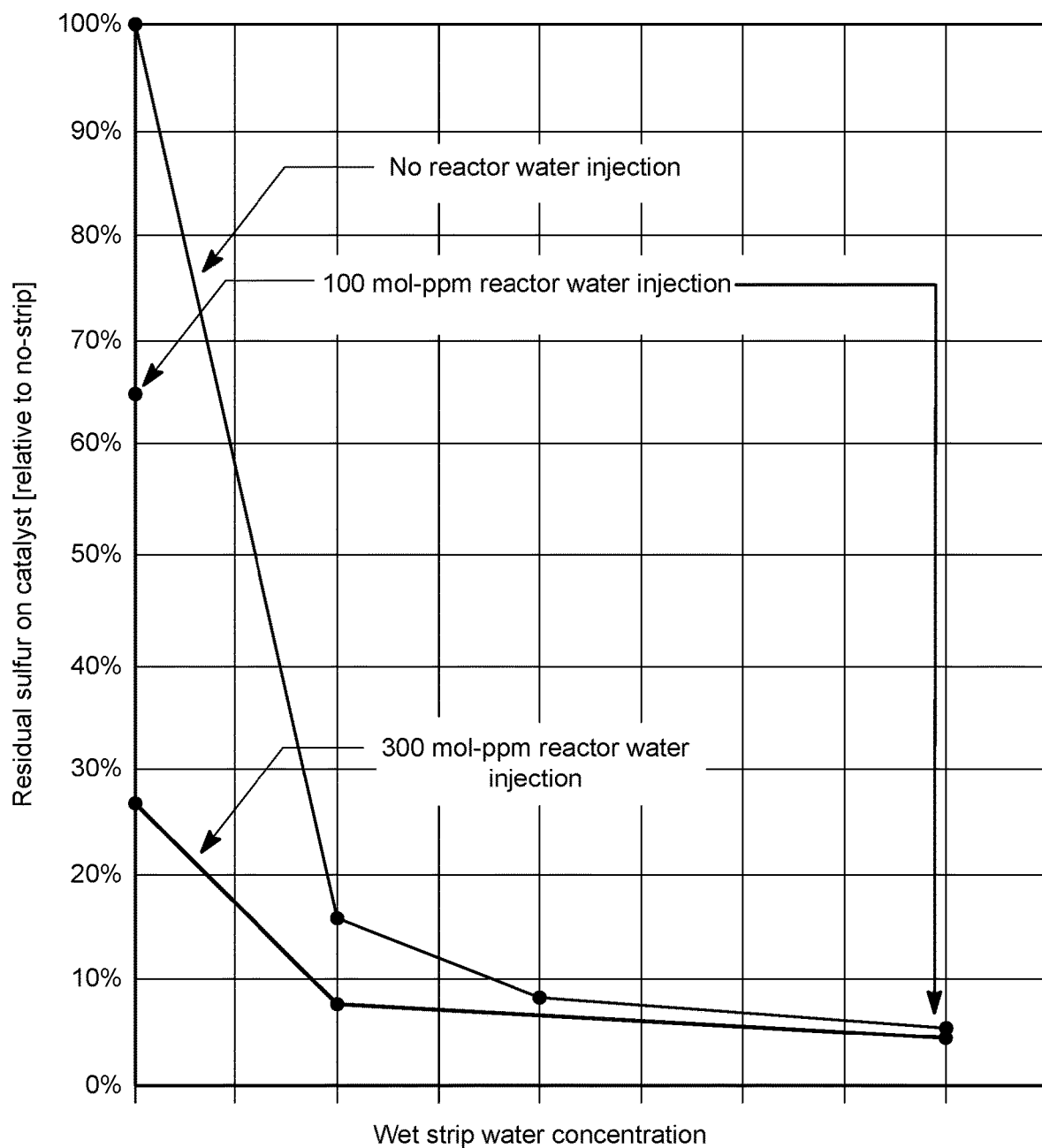
FIG. 3 illustrates the effects of water injection to the stripper and the reactor.

FIG. 3 demonstrates the benefits of the process claimed in this invention. The points on the Y axis demonstrate the percentage of sulfur on the catalyst when there is no water in the stripper. The sulfur level drops when there is water injected into the reactors. However, the points that move along the X axis demonstrate how the sulfur level decreases as water is injected in to the stripper, as well. The sulfur level decreases as more water is injected into the reactors, the stripper, and both the reactors and the stripper.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims. In the foregoing, all temperatures are set forth in degrees Celsius and, all parts and percentages are by weight, unless otherwise indicated.

SPECIFIC EMBODIMENTS

While the following is described in conjunction with specific embodiments, it will be understood that this description is intended to illustrate and not limit the scope of the preceding description and the appended claims.

A first embodiment of the invention is a process for regenerating a spent catalyst from a reactor comprising a. passing the spent catalyst, having sulfur on the catalyst, to a sulfur stripping vessel; b. injecting a water stream into a gas stream; c. passing the hydrogen gas stream to the stripping vessel at an elevated temperature, thereby generating a stripped spent catalyst stream; d. passing the spent catalyst stream to a regenerator, thereby generating a regenerated catalyst stream; and e. returning the regenerated catalyst to the reactor section via the reduction zone. An embodiment of the invention is one, any or all of prior embodiments in this paragraph up through the first embodiment in this paragraph wherein the gas stream comprises hydrogen. An embodiment of the invention is one, any or all of prior embodiments in this paragraph up through the first embodiment in this paragraph wherein the water stream comprises stream. An embodiment of the invention is one, any or all of prior embodiments in this paragraph up through the first embodiment in this paragraph wherein the water stream comprises condensate. An embodiment of the invention is one, any or all of prior embodiments in this paragraph up through the first embodiment in this paragraph wherein the water stream comprises demineralized steam or water. An embodiment of the invention is one, any or all of prior embodiments in this paragraph up through the first embodiment in this paragraph further comprising passing the stripped spent catalyst stream to a catalyst cooler prior to passing the catalyst to the regenerator. An embodiment of the invention is one, any or all of prior embodiments in this paragraph up through the first embodiment in this paragraph wherein at least 50% of the sulfur on the spent catalyst is removed in the sulfur stripping vessel. An embodiment of the invention is one, any or all of prior embodiments in this paragraph up through the first embodiment in this paragraph wherein the gas is passed at a temperature between about 100° C. and about 200° C. An embodiment of the invention is one, any or all of prior embodiments in this paragraph up through the first embodiment in this paragraph wherein the gas is passed at a temperature between about 100° C. and about 150° C. An embodiment of the invention is one, any or all of prior embodiments in this paragraph up through the first embodiment in this paragraph wherein the stripping vessel temperature is at least 150° C. An embodiment of the invention is one, any or all of prior embodiments in this paragraph up through the first embodiment in this paragraph wherein the stripping vessel temperature is at least 250° C. An embodiment of the invention is one, any or all of prior embodiments in this paragraph up through the first embodiment in this paragraph wherein the reactor is a dehydrogenation reactor, and the catalyst is a dehydrogenation catalyst.

A second embodiment of the invention is a process for managing sulfur in a catalytic process comprising a. passing a spent dehydrogenation catalyst stream to a stripping and cooling vessel; b. injecting a water stream into a sulfur free hydrogen rich gas stream; c. passing the hydrogen rich gas to the stripping and cooling vessel, stripping the catalyst of sulfur, thereby generating a stripped spent dehydrogenation catalyst that passes to the cooling section of the stripping and cooling vessel; d. passing a gas to the stripping and cooling vessel to cool the stripped catalyst, thereby generating a cooled catalyst stream; e. passing the cooled catalyst to a regenerator, to generate a regenerated catalyst; and f. passing the regenerated catalyst to a dehydrogenation reactor section. An embodiment of the invention is one, any or all of prior embodiments in this paragraph up through the second embodiment in this paragraph wherein at least 50% of the sulfur on the spent catalyst is removed in the sulfur stripping vessel. An embodiment of the invention is one, any or all of prior embodiments in this paragraph up through the second embodiment in this paragraph wherein the elevated temperature of the hydrogen gas is at least 300° C. An embodiment of the invention is one, any or all of prior embodiments in this paragraph up through the second embodiment in this paragraph wherein the gas is passed at a temperature between about 100° C. and about 200° C.

A third embodiment of the invention is a process for regenerating a spent catalyst from a reactor comprising a. passing a first feed stream to a first reactor to produce a first effluent stream; b. passing the first effluent stream to a second reactor to produce a second effluent stream; c. passing the second effluent stream to a third reactor to produce a third effluent stream; d. passing the spent catalyst stream to a regenerator, thereby generating a regenerated catalyst stream; and e. returning the regenerated catalyst to the reactor section via the reduction zone. An embodiment of the invention is one, any or all of prior embodiments in this paragraph up through the first embodiment in this paragraph further comprising passing the third effluent stream to a fourth reactor to produce a product stream; passing the spent catalyst from the fourth reactor having sulfur on the catalyst, to a sulfur stripping vessel; passing a hydrogen gas stream to the stripping vessel at an elevated temperature, thereby generating a stripped spent catalyst stream; passing the spent catalyst stream to a regenerator, thereby generating a regenerated catalyst stream; and returning the regenerated catalyst to the reactor section via the reduction zone. An embodiment of the invention is one, any or all of prior embodiments in this paragraph up through the first embodiment in this paragraph further comprising a water stream that is injected into the inlet of any of the reactors. An embodiment of the invention is one, any or all of prior embodiments in this paragraph up through the first embodiment in this paragraph wherein the spent catalyst stream passes from the last reactor to a sulfur stripping vessel. An embodiment of the invention is one, any or all of prior embodiments in this paragraph up through the first embodiment in this paragraph wherein the water stream comprises stream. An embodiment of the invention is one, any or all of prior embodiments in this paragraph up through the first embodiment in this paragraph wherein the water stream comprises condensate. An embodiment of the invention is one, any or all of prior embodiments in this paragraph up through the first embodiment in this paragraph wherein the water stream comprises demineralized steam or water. An embodiment of the invention is one, any or all of prior embodiments in this paragraph up through the first embodiment in this paragraph further comprising passing the stripped spent catalyst stream to a catalyst cooler prior to passing the catalyst to the regenerator. An embodiment of the invention is one, any or all of prior embodiments in this paragraph up through the first embodiment in this paragraph wherein at least 50% of the sulfur on the spent catalyst is removed in the sulfur stripping vessel. An embodiment of the invention is one, any or all of prior embodiments in this paragraph up through the first embodiment in this paragraph wherein the stripping vessel temperature is at least 150° C. An embodiment of the invention is one, any or all of prior embodiments in this paragraph up through the first embodiment in this paragraph wherein the stripping vessel temperature is at least 250° C. An embodiment of the invention is one, any or all of prior embodiments in this paragraph up through the first embodiment in this paragraph wherein the reduction zone removes halogen compounds from the catalyst. An embodiment of the invention is one, any or all of prior embodiments in this paragraph up through the first embodiment in this paragraph wherein the halogen removed is chloride.

A fourth embodiment of the invention is a process for regenerating a spent catalyst from a reactor comprising a. passing a first feed stream and a first water stream to a first reactor to produce a first effluent stream; b. passing the first effluent product stream and a second water stream to a second reactor to produce a second effluent stream; c. passing the second effluent stream and a third water stream to a third reactor to produce a third effluent stream; d. passing the third effluent stream and a fourth water stream to a fourth reactor to product a product stream; e. passing the spent catalyst from the fourth reactor having sulfur on the catalyst, to a sulfur stripping vessel; f passing a hydrogen gas stream to the stripping vessel at an elevated temperature, thereby generating a stripped spent catalyst stream; g. passing the spent catalyst stream to a regenerator, thereby generating a regenerated catalyst stream; and h. returning the regenerated catalyst to the reactor section via the reduction zone. An embodiment of the invention is one, any or all of prior embodiments in this paragraph up through the second embodiment in this paragraph wherein the water stream comprises stream. An embodiment of the invention is one, any or all of prior embodiments in this paragraph up through the second embodiment in this paragraph wherein the water stream comprises condensate. An embodiment of the invention is one, any or all of prior embodiments in this paragraph up through the second embodiment in this paragraph wherein the water stream comprises demineralized steam or water. An embodiment of the invention is one, any or all of prior embodiments in this paragraph up through the second embodiment in this paragraph further comprising a. passing the stripped spent catalyst to a cooling zone, to generate a cooled spent catalyst and a cooling zone effluent gas; and b. passing the cooled spent catalyst to the regenerator.

A fifth embodiment of the invention is a process for regenerating a spent catalyst from a reactor comprising a. passing a first feed stream to a first reactor to produce a first effluent stream; b. passing the first effluent stream to a second reactor to produce a second effluent stream; c. passing the second effluent stream to a third reactor to produce a third effluent stream; d. passing the third effluent stream and a water stream to a fourth reactor to product a product stream; e. passing the spent catalyst from the fourth reactor having sulfur on the catalyst, to a sulfur stripping vessel; f. passing a hydrogen gas stream to the stripping vessel at an elevated temperature, thereby generating a stripped spent catalyst stream; g. passing the spent catalyst stream to a regenerator, thereby generating a regenerated catalyst stream; and h. returning the regenerated catalyst to the reactor section via the reduction zone. An embodiment of the invention is one, any or all of prior embodiments in this paragraph up through the third embodiment in this paragraph wherein the water stream comprises stream, condensate, or demineralized stream or water.

A sixth embodiment of the invention is a process for regenerating a spent catalyst from a reactor comprising a. passing a first feed stream to a first reactor to produce a first effluent stream; b. passing the first effluent stream to a second reactor to produce a second effluent stream; c. passing the second effluent stream to a third reactor to produce a third effluent stream; d. passing the third effluent stream to a fourth reactor to product a product stream; e. passing the spent catalyst from the fourth reactor having sulfur on the catalyst, to a sulfur stripping vessel; f injecting a water stream into a hydrogen gas stream; g. passing a hydrogen gas stream to the stripping vessel at an elevated temperature, thereby generating a stripped spent catalyst stream; h. passing the spent catalyst stream to a regenerator, thereby generating a regenerated catalyst stream; and i. returning the regenerated catalyst to the reactor section via the reduction zone. An embodiment of the invention is one, any or all of prior embodiments in this paragraph up through the first embodiment in this paragraph further comprising a water stream that is injected into the inlet of any of the four reactors. An embodiment of the invention is one, any or all of prior embodiments in this paragraph up through the first embodiment in this paragraph wherein the water stream comprises stream. An embodiment of the invention is one, any or all of prior embodiments in this paragraph up through the first embodiment in this paragraph wherein the water stream comprises condensate. An embodiment of the invention is one, any or all of prior embodiments in this paragraph up through the first embodiment in this paragraph wherein the water stream comprises demineralized steam or water. An embodiment of the invention is one, any or all of prior embodiments in this paragraph up through the first embodiment in this paragraph further comprising passing the stripped spent catalyst stream to a catalyst cooler prior to passing the catalyst to the regenerator. An embodiment of the invention is one, any or all of prior embodiments in this paragraph up through the first embodiment in this paragraph wherein at least 50% of the sulfur on the spent catalyst is removed in the sulfur stripping vessel. An embodiment of the invention is one, any or all of prior embodiments in this paragraph up through the first embodiment in this paragraph wherein the stripping vessel temperature is at least 150° C. An embodiment of the invention is one, any or all of prior embodiments in this paragraph up through the first embodiment in this paragraph wherein the stripping vessel temperature is at least 250° C. An embodiment of the invention is one, any or all of prior embodiments in this paragraph up through the first embodiment in this paragraph wherein the reduction zone removes halogen compounds from the catalyst. An embodiment of the invention is one, any or all of prior embodiments in this paragraph up through the first embodiment in this paragraph wherein the halogen removed is chloride.

A seventh embodiment of the invention is a process for regenerating a spent catalyst from a reactor comprising a. passing a first feed stream and a first water stream to a first reactor to produce a first effluent stream; b. passing the first effluent stream and a second water stream to a second reactor to produce a second effluent stream; c. passing the second effluent stream and a third water stream to a third reactor to produce a third effluent stream; d. passing the third effluent stream and a fourth water stream to a fourth reactor to product a product stream; e. passing the spent catalyst from the fourth reactor having sulfur on the catalyst, to a sulfur stripping vessel; f injecting a water stream into a hydrogen gas stream; g. passing a hydrogen gas stream to the stripping vessel at an elevated temperature, thereby generating a stripped spent catalyst stream; h. passing the spent catalyst stream to a regenerator, thereby generating a regenerated catalyst stream; and i. returning the regenerated catalyst to the reactor section via the reduction zone. An embodiment of the invention is one, any or all of prior embodiments in this paragraph up through the second embodiment in this paragraph wherein the water stream comprises stream. An embodiment of the invention is one, any or all of prior embodiments in this paragraph up through the second embodiment in this paragraph wherein the water stream comprises condensate. An embodiment of the invention is one, any or all of prior embodiments in this paragraph up through the second embodiment in this paragraph wherein the water stream comprises demineralized steam or water. An embodiment of the invention is one, any or all of prior embodiments in this paragraph up through the second embodiment in this paragraph further comprising a. passing the stripped spent catalyst to a cooling zone, to generate a cooled spent catalyst and a cooling zone effluent gas; and b. passing the cooled spent catalyst to the regenerator.

An eighth embodiment of the invention is a process for regenerating a spent catalyst from a reactor comprising a. passing a first feed stream to a first reactor to produce a first effluent stream; b. passing the first effluent stream to a second reactor to produce a second effluent stream; c. passing the second effluent stream to a third reactor to produce a third effluent stream; d. passing the spent catalyst from the third reactor having sulfur on the catalyst, to a sulfur stripping vessel; e. passing a hydrogen gas stream to the stripping vessel at an elevated temperature, thereby generating a stripped spent catalyst stream; f. passing the spent catalyst stream to a regenerator, thereby generating a regenerated catalyst stream; and g. returning the regenerated catalyst to the reactor section via the reduction zone. An embodiment of the invention is one, any or all of prior embodiments in this paragraph up through the third embodiment in this paragraph wherein the water stream comprises stream. An embodiment of the invention is one, any or all of prior embodiments in this paragraph up through the third embodiment in this paragraph wherein the water stream comprises condensate. An embodiment of the invention is one, any or all of prior embodiments in this paragraph up through the third embodiment in this paragraph wherein the water stream comprises demineralized steam or water.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims. In the foregoing, all temperatures are set forth in degrees Celsius and, all parts and percentages are by weight, unless otherwise indicated.

The invention claimed is:

1. A process for regenerating a spent catalyst from a reactor comprising:
   (a) passing the spent catalyst, having sulfur on the catalyst, to a sulfur stripping vessel;
   (b) injecting a water stream into a gas stream to generate a hydrogen gas stream consisting essentially of hydrogen and water;
   (c) passing the hydrogen gas stream to the sulfur stripping vessel at an elevated temperature, thereby generating a stripped spent catalyst stream;
   (d) passing the stripped spent catalyst stream to a regenerator wherein the stripped spent catalyst stream is contacted with chlorine-containing gas, thereby generating a regenerated catalyst stream; and
   (e) returning the regenerated catalyst to the reactor via a reduction zone.

2. The process of claim 1 wherein the gas stream comprises hydrogen.

3. The process of claim 1 wherein the water stream comprises steam.

4. The process of claim 1 wherein the water stream comprises condensate.

5. The process of claim 1 wherein the water stream comprises demineralized steam or water.

6. The process of claim 1 further comprising passing the stripped spent catalyst stream to a catalyst cooler prior to passing the catalyst to the regenerator.

7. The process of claim 1 wherein at least 50% of the sulfur on the spent catalyst is removed in the sulfur stripping vessel.

8. The process of claim 6 wherein the catalyst is cooled to a temperature between about 100° C. and about 200° C.

9. The process of claim 6 wherein the catalyst is cooled to a temperature between about 100° C. and about 150° C.

10. The process of claim 1 wherein the sulfur stripping vessel temperature is at least 150° C.

11. The process of claim 1 wherein the sulfur stripping vessel temperature is at least 250° C.

12. The process of claim 1 wherein the reactor is a dehydrogenation reactor, and the spent catalyst is a spent dehydrogenation catalyst.

13. A process for managing sulfur in a catalytic process comprising:
   (a) passing a spent dehydrogenation catalyst stream to a stripping and cooling vessel;
   (b) injecting a water stream into a sulfur free hydrogen gas stream to generate a hydrogen gas stream consisting essentially of hydrogen and water;
   (c) passing the hydrogen gas stream to the stripping and cooling vessel, stripping the spent dehydrogenation catalyst of sulfur, thereby generating a stripped spent dehydrogenation catalyst that passes to a cooling zone of the stripping and cooling vessel;
   (d) passing a gas to the stripping and cooling vessel to cool the stripped spent dehydrogenation catalyst, thereby generating a cooled catalyst stream;
   (e) passing the cooled catalyst stream to a regenerator wherein the cooled catalyst stream is contacted with chlorine-containing gas, to generate a regenerated catalyst; and
   (f) passing the regenerated catalyst to a dehydrogenation reactor section.

14. The process of claim 13 wherein at least 50% of the sulfur on the spent dehydrogenation catalyst is removed in the stripping and cooling vessel.

15. The process of claim 13 wherein the hydrogen gas stream is at a temperature of at least 300° C.

16. The process of claim 13 wherein the gas is passed at a temperature between about 100° C. and about 200° C.

17. The process of claim 13 wherein the gas is passed at a temperature between about 100° C. and about 150° C.

* * * * *